United States Patent
Chang et al.

(10) Patent No.: US 9,959,617 B2
(45) Date of Patent: May 1, 2018

(54) MEDICAL IMAGE PROCESSING APPARATUS AND BREAST IMAGE PROCESSING METHOD THEREOF

(71) Applicant: TAIHAO MEDICAL INC., Taipei (TW)

(72) Inventors: Ruey-Feng Chang, Taichung (TW); Rong-Tai Chen, Taichung (TW); Hsin-Hung Lai, Taipei (TW); Hong-Hao Chen, Hsinchu (TW)

(73) Assignee: TAIHAO MEDICAL INC., Taipei (TW)

( * ) Notice: Subject to any disclaimer, the term of this patent is extended or adjusted under 35 U.S.C. 154(b) by 1 day.

(21) Appl. No.: 15/215,607

(22) Filed: Jul. 21, 2016

(65) Prior Publication Data

US 2017/0221201 A1  Aug. 3, 2017

(30) Foreign Application Priority Data

Jan. 28, 2016 (TW) .............................. 105102753 A
Apr. 21, 2016 (TW) .............................. 105112377 A (51) Int. Cl.
*G06T 7/00* (2017.01)
*A61B 5/055* (2006.01)
(Continued)

(52) U.S. Cl.
CPC ............ *G06T 7/0012* (2013.01); *A61B 5/055* (2013.01); *A61B 6/502* (2013.01); *A61B 8/0825* (2013.01);
(Continued)

(58) Field of Classification Search
USPC ........................................................ 382/128
See application file for complete search history.

(56) References Cited

U.S. PATENT DOCUMENTS 8,340,380 B2    12/2012  Morita
8,600,126 B2 *  12/2013  Morita ................... G06T 5/008
                                              382/128
(Continued)

FOREIGN PATENT DOCUMENTS

CN      104182965      12/2014
TW      201415012       4/2014
(Continued)

OTHER PUBLICATIONS

"Office Action of Taiwan Counterpart Application," dated Dec. 12, 2016, p. 1-p. 7, in which the listed references were cited.

*Primary Examiner* — Ishrat I Sherali
(74) *Attorney, Agent, or Firm* — JCIPRNET (57) ABSTRACT

A medical image processing apparatus and a breast image processing method thereof are provided. The processing method at least contains but not limited to the following steps. At least one slice of breast image is obtained. Mammary glandular tissue in each breast image is detected through a mammary glandular tissue detector. The mammary glandular tissue detector is based on texture characteristic analysis. Therefore, the embodiments of the present disclosure would assist density analysis of the mammary glandular tissue and efficiently reduce false positive of computer-aided detection. In addition, based on a result of the density analysis of the mammary glandular tissue, the embodiment would further determine lactation yield and present density diagrams of mammary glandular tissue of left and right breasts. A breast region may also be separated from the breast image based on rib information according to the embodiments of the present disclosure.

9 Claims, 8 Drawing Sheets

(51) Int. Cl.
   *A61B 6/00*    (2006.01)
   *A61B 8/08*    (2006.01)
   *G06N 99/00*   (2010.01)
   *G06T 7/45*    (2017.01)

(52) U.S. Cl.
   CPC ............ *G06N 99/005* (2013.01); *G06T 7/45* (2017.01); *G06T 2207/10004* (2013.01); *G06T 2207/20081* (2013.01); *G06T 2207/30068* (2013.01)

(56) References Cited

U.S. PATENT DOCUMENTS

| | | | |
|---|---|---|---|
| 9,619,879 B2 * | 4/2017 | Seong | G06T 7/0012 |
| 2009/0252396 A1 | 10/2009 | Morita | |
| 2010/0280375 A1 | 11/2010 | Zhang et al. | |
| 2012/0014578 A1 | 1/2012 | Karssemeijer et al. | |
| 2013/0030278 A1 * | 1/2013 | Seong | G06T 7/0012 |
| | | | 600/407 |
| 2015/0003702 A1 * | 1/2015 | Serlie | A61B 5/7275 |
| | | | 382/128 |
| 2015/0087979 A1 | 3/2015 | Zhang et al. | |
| 2015/0230773 A1 | 8/2015 | Cho et al. | |

FOREIGN PATENT DOCUMENTS

| | | |
|---|---|---|
| TW | 201445139 | 12/2014 |
| TW | I483711 | 5/2015 |

* cited by examiner

MEDICAL IMAGE PROCESSING APPARATUS AND BREAST IMAGE PROCESSING METHOD THEREOF

CROSS-REFERENCE TO RELATED APPLICATION

This application claims the priority benefit of Taiwan application serial no. 105102753, filed on Jan. 28, 2016, and Taiwan application serial no. 105112377, filed on Apr. 21, 2016. The entirety of each of the above-mentioned patent applications is hereby incorporated by reference herein and made a part of this specification.

BACKGROUND OF THE INVENTION

1. Field of the Invention

The present disclosure relates to an image processing technique, and particularly relates to a medical image processing apparatus and a breast image processing method thereof.

2. Description of Related Art

Mammary carcinoma is one of the most common malignant tumors in woman, and the main symptoms include breast tumor, abnormal secretions, or shape variation, etc. To early screen the abnormal breast symptoms avails treating the tumor as early as possible, so as to decrease a chance of deterioration or proliferation of cancer cells. Screening methods such as clinical or self breast detection, biopsy, mammography, ultrasound, or magnetic resonance imaging, etc., have been widely used in clinical practice or become important issues in academic researches.

According to researches, it is known that compared to a low density breast, women with a high density breast has a high risk of suffering from breast cancer. Therefore, density analysis on breast and mammary glandular tissues is also an important factor in breast cancer assessment. On the other hand, although a computer-aided detection (CADe) system has been used in clinical practice to automatically identify tumors, lumps, or calcifications, it still has a high risk of false positive.

SUMMARY OF THE INVENTION

The disclosure is directed to a medical image processing apparatus and a breast image processing method thereof, which assists density analysis of mammary glandular tissue and efficiently reduces false positive of a computer-aided detection system.

The disclosure provides a breast image processing method, which is adapted to a medical image processing apparatus, and at least includes (but not limited to) following steps. At least one slice of breast image is obtained. Mammary glandular tissue in each breast image is detected through a mammary glandular tissue detector. The mammary glandular tissue detector is based on texture characteristic analysis.

In an embodiment of the present disclosure, after the breast image is obtained, the method further includes the following steps. The breast image in a first view is transformed into at least one perspective-shifted breast image in a second view. The first view is different from the second view. Rib information is determined according to the at least one perspective-shifted breast image. A breast region in the perspective-shifted breast image is determined according to the rib information.

According to another aspect, the present disclosure provides a medical image processing apparatus, which at least includes (but not limited to) a storage unit and a processing unit. The storage unit stores at least one slice of breast image, and records a plurality of modules. The processing unit is coupled to the storage unit, and accesses and executes the modules recorded in the storage unit. The modules include an image input module and a mammary glandular detection module. The image input module obtains the at least one breast image. The mammary glandular detection module detects mammary glandular tissue in each breast image through a mammary glandular tissue detector. The mammary glandular tissue detector is based on texture characteristic analysis.

According to the above descriptions, the medical image processing apparatus and a breast image processing method thereof of the present disclosure may detect the mammary glandular tissue in the breast image based on texture characteristic analysis. In this way, the embodiments of the present disclosure may improve accuracy for detecting the mammary glandular tissue, and assist density analysis of the mammary glandular tissue and efficiently reduce false positive of the computer-aided detection system.

In order to make the aforementioned and other features and advantages of the present disclosure comprehensible, several exemplary embodiments accompanied with figures are described in detail below.

BRIEF DESCRIPTION OF THE DRAWINGS

The accompanying drawings are included to provide a further understanding of the present disclosure, and are incorporated in and constitute a part of this specification. The drawings illustrate embodiments of the present disclosure and, together with the description, serve to explain the principles of the present disclosure.

DESCRIPTION OF THE EMBODIMENTS

Reference will now be made in detail to the present preferred embodiments of the present disclosure, examples of which are illustrated in the accompanying drawings. Wherever possible, the same reference numbers are used in the drawings and the description to refer to the same or like parts.

Figure 1:
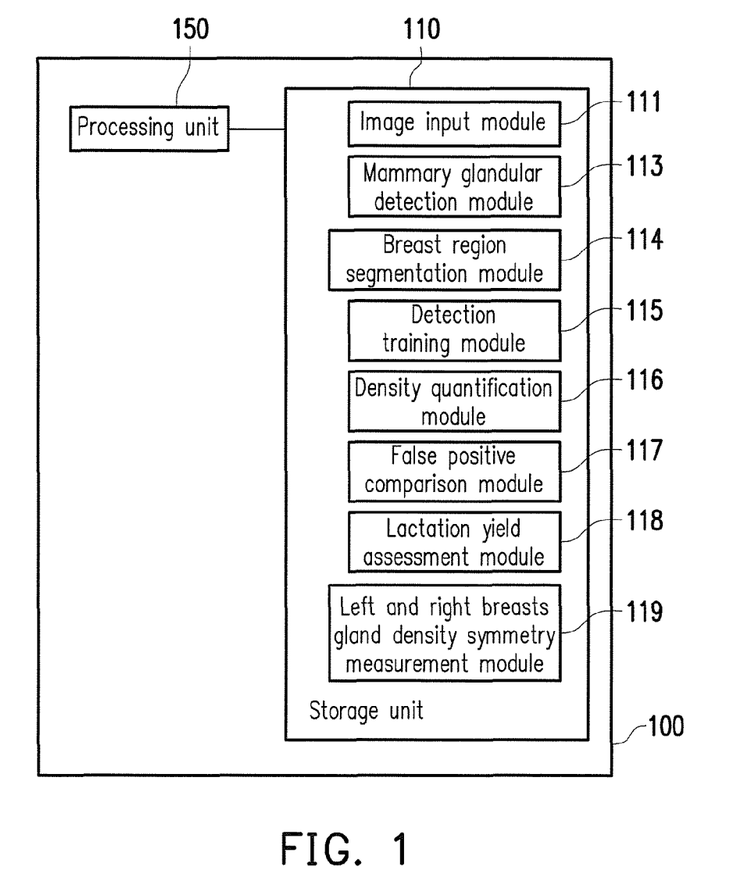
FIG. 1 is a block diagram of a medical image processing apparatus according to an embodiment of the present disclosure.

FIG. 1 is a block diagram of a medical image processing apparatus according to an embodiment of the present disclosure. Referring to FIG. 1, the medical image processing apparatus 100 at least includes (but not limited to) a storage unit 110 and a processing unit 150. The medical image processing apparatus 100 can be an electronic apparatus such as a server, a user device, a desktop computer, a notebook, a network computer, a working station, a personal digital assistant (PDA), a personal computer (PC), etc., which is not limited by the present disclosure.

The storage unit 110 may be a fixed or a movable device in any possible forms including a random access memory (RAM), a read-only memory (ROM), a flash memory or other similar devices, or a combination of the above-mentioned devices. In the present embodiment, the storage unit 110 is used for storing at least one slice of breast image and breast training image, a program code, a device configuration, buffer or permanent data, and records software programs such as an image input module 111, a mammary glandular detection module 113, a breast region segmentation module 114, a detection training module 115, a density quantification module 116, a false positive comparison module 117, a lactation yield assessment module 118, left and right breasts gland density symmetry measurement module 119, etc. The processing unit 150 can access and execute afore-mentioned modules, and operation details thereof will be described later in following embodiments. The storage unit 110 of the present embodiment is not limited to be a single memory device, and the aforementioned software modules can also be separately stored in two or more memory devices of the same type or different types.

Functions of the processing unit 150 can be implemented by using a programmable unit such as a central processing unit (CPU), a microprocessor, a micro controller, a digital signal processing (DSP) chip, a field programmable gate array (FPGA), etc. The functions of the processing unit 150 can be implemented by using an independent electronic device or integrated circuit (IC), and the processing unit 150 can also be implemented in a hardware or software manner.

In order to facilitate understanding an operation flow of the embodiment of the present disclosure, a plurality of embodiments is provided below to describe a flow that the medical image processing apparatus 100 of the present embodiment performs breast image processing in detail.

Figure 2:
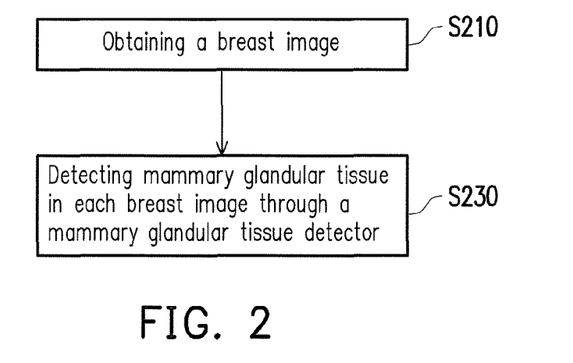
FIG. 2 is a flowchart illustrating a breast image processing method according to an embodiment of the present disclosure.

FIG. 2 is a flowchart illustrating a breast image processing method according to an embodiment of the present disclosure. Referring to FIG. 2, the method of the present embodiment is adapted to the medical image processing apparatus 100 of FIG. 1. The method of the present embodiment is described below with reference of various components and modules of the medical image processing apparatus 100. Various steps of the method can be adjusted according to an actual implementation requirement, which is not limited by the present disclosure.

In step S210, the image input module 111 obtains at least one slice of breast image. The breast image can be a two-dimensional (2D) or three-dimensional (3D) medical image of the breast based on automated breast ultrasound (ABUS), digital breast tomosynthesis (DBT), magnetic resonance imaging (MRI), etc. In screening, the 3D image technique may provide a reliable breast density assessment for cancer risk, though the present disclosure is not limited to the 3D image.

The image input module 111 may obtain the breast image from the storage unit 110, through a wireless or wired communication unit (for example, Wi-Fi, Ethernet), a medical image scanner (for example, an ABUS scanner, a MRI scanner, etc.), or from a storage device (for example, a DVD, a flash drive, a hard disk, etc.).

In step S230, the mammary glandular detection module 113 detects mammary glandular tissue in each breast image through a mammary glandular tissue detector. The mammary glandular tissue detector is based on texture characteristic analysis. In the present embodiment, the detection training module 115 may train the mammary glandular tissue detector based on texture characteristic analysis.

To be specific, before the mammary glandular detection module 113 performs detection through the mammary glandular tissue detector, the detection training module 115 may train the mammary glandular tissue detector according to a plurality of breast training images. The detection training module 115 may separate the content of the breast training images into a plurality of characteristic types. The characteristic types at least include (but not limited to) a mammary glandular tissue type, subcutaneous fat type, a retromammary fat and pectoralis muscle type, and a shadow type.

Figure 3:
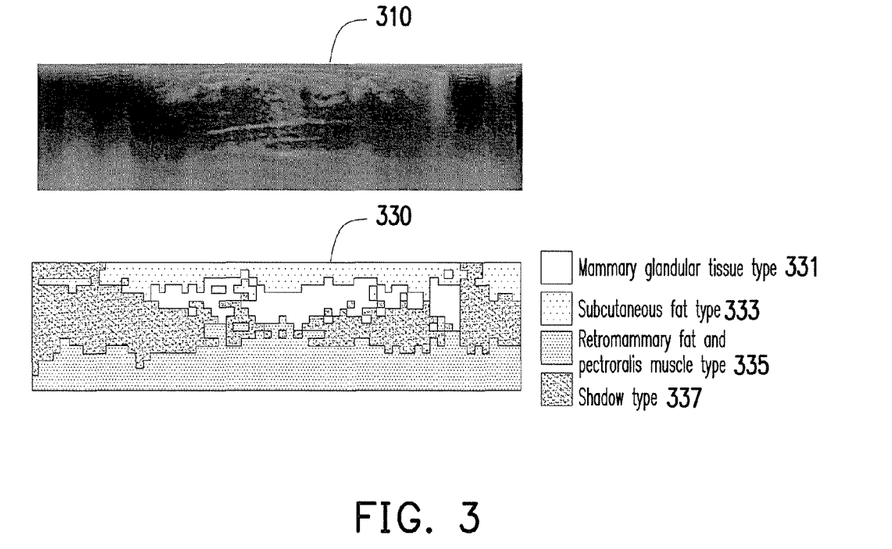
FIG. 3 is an example of separating types.

FIG. 3 is an example of separating types. Referring to FIG. 3, the medical image processing apparatus 100 may display a breast training image 310 through a display unit (for example, a liquid crystal display (LCD), a plasma display panel (PDP), an organic light emitting diode (OLED), etc.), and provide an input unit (for example, a touch device, a keyboard, a mouse, etc.) to receive a separating operation of the user on the breast training image 310. The detection training module 115 may detect the characteristic types corresponding to the separating operation and a selected region (or location) on the breast training image 310. A breast training image 330 is an image obtained after the characteristic type separation, which may include a mammary glandular tissue type 331, a subcutaneous fat type 333, a retromammary fat and pectoralis muscle type 335, and a shadow type 337.

Figure 4:
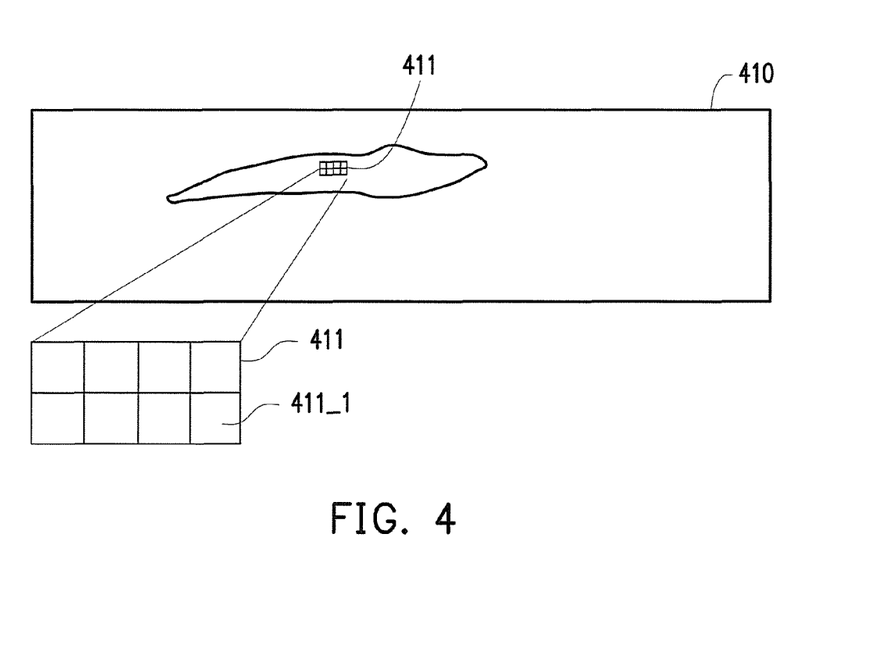
FIG. 4 is an example of image blocks.

The detection training module 115 performs the texture characteristic analysis on a plurality of image blocks in the breast training images. The detection training module 115 may first define a unit size (for example, 11*11, 12*12 or 15*20 pixels, etc.) of each image block. For example, FIG. 4 is an example of the image blocks. Referring to FIG. 4, in a partial image 411 in a breast training image 410, 11*11 pixels can be taken as the unit size of the image block (for example, the image block 411_1).

Then, the detection training module 115 extracts texture characteristics from each of the image blocks in each of the breast training images. For example, the detection training module 115 may use a gray-level co-occurrence matrix (GLCM) method to obtain the mean and standard deviation of each GLCM texture characteristics including energy, entropy, correlation, difference moment, inertia, cluster shade, cluster prominence, Haralick's correlation or a combination thereof. It should be noted that the detection training module 115 may also use any texture characteristic related algorithm such as Markov random field (MRF), Gabor filter, etc., to extract the required texture characteristics, which is not limited by the present disclosure.

The detection training module 115 trains a classifier based on the texture characteristic analysis of each image block for the characteristic types. In other words, the detection training module 115 may determine whether the image block corresponding to the extracted texture characteristics belongs to the mammary glandular tissue type, the subcutaneous fat type, the retromammary fat and pectoralis muscle type, or the shadow type, and train the classifier via the corresponding texture characteristics for different characteristic types.

In the present embodiment, the detection training module 115 may use (but not limited to) logistic regression, support vector machine (SVM), neural network (NN), etc., to train the classifier based on the texture characteristics extracted from each image block.

Figure 5:
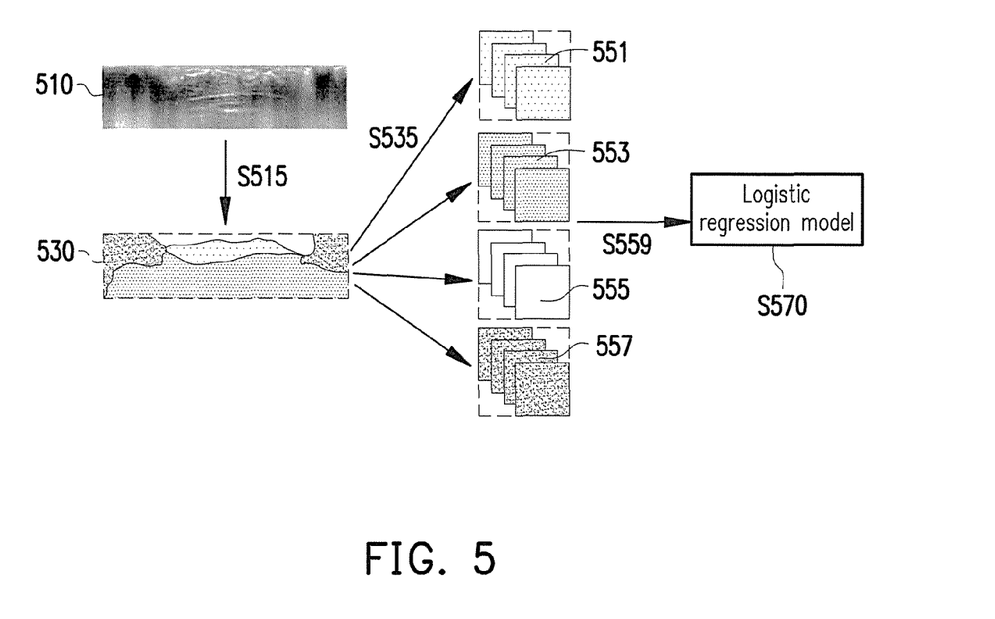
FIG. 5 is a schematic diagram of a flow for training a classifier.

For example, FIG. 5 is a schematic diagram of a flow for training the classifier. Referring to FIG. 5, the detection training module 115 obtains a breast training image 510, and generates a breast training image 530 according to a separating operation of the characteristic types performed by the user (step S515). In the breast training image 530, different characteristic types are represented by different background colors. In step S535, the detection training module 115 classifies image blocks corresponding to different characteristic types to generate image block groups 551, 553, 555, and 557 respectively corresponding to the mammary glandular tissue type, the subcutaneous fat type, the retromammary fat and pectoralis muscle type, and the shadow type. Each of the image block groups 551 to 557 may have one or more image blocks, and the image blocks of the same characteristic type belong to the same image block group. In step S559, the detection training module 115 extracts texture characteristics of each of the image block groups 551 to 557. In step S570, the detection training module 115 trains the classifier capable of separating different characteristic types through a logistic regression model.

In the present embodiment, the detection training module 115 may take the classifier for the mammary glandular tissue type as the mammary glandular tissue detector. In other words, the classifier trained by the detection training module 115 may serve as a detector of the characteristic types such as the mammary glandular tissue type, the subcutaneous fat type, the retromammary fat and pectoralis muscle type, and the shadow type.

Figure 6:
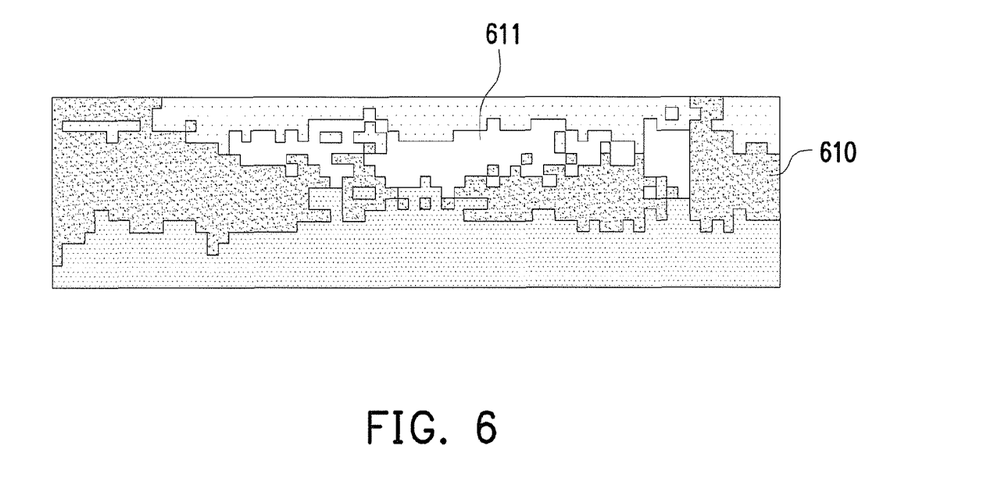
FIG. 6 is an example of mammary glandular tissue detection.

After the mammary glandular tissue detector is trained, the mammary glandular detection module 113 may detect the breast image obtained by the image input module 111 through the mammary glandular tissue detector. The mammary glandular detection module 113 may use the texture characteristic related algorithm adopted by the detection training module 115 to extract the texture characteristics of all of or a part of the image blocks in each slice of breast image, and compare the similarity with the texture characteristics recorded by the detection training module 115 through the classifier, so as to classify the image blocks. For example, FIG. 6 is an example of mammary glandular tissue detection. Referring to FIG. 6, an image region 611 (presented in the white background color) in a breast image 610 is a region of the mammary glandular tissue detected by the mammary glandular tissue detector.

Since the mammary glandular tissue detector takes image block as the unit size (for example, 11*11, 12*12 or 15*20 pixels, etc.) to perform classification, the breast image classified by the classifier is presented in image blocks (for example, the breast image 610 of FIG. 6 is composed of a plurality of image blocks). In an embodiment, the mammary glandular detection module 113 further performs image post processing on the classified breast image, so as to adjust a shape of the mammary glandular tissue.

Figure 7:
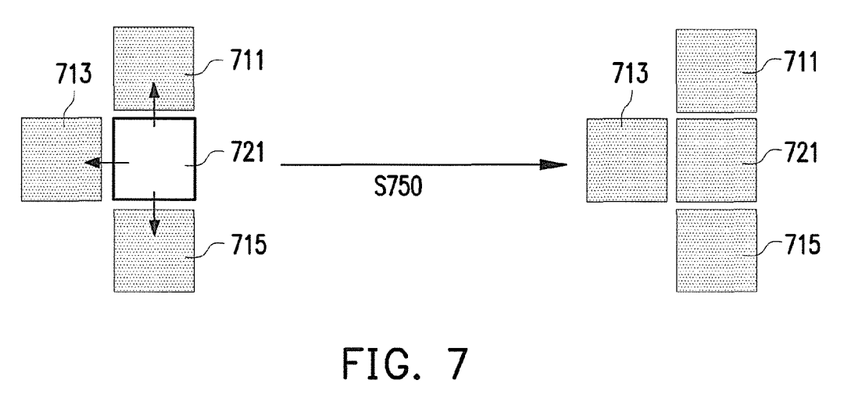
FIG. 7 is an example of filling up the mammary glandular tissue.

The mammary glandular detection module 113 may fill up at least one cavity of the mammary glandular tissue in the breast image classified by the classifier. The mammary glandular detection module 113 determines whether at least two second image blocks classified to the mammary glandular tissue type exist adjacent to a first image block. For example, FIG. 7 is an example of filling up the mammary glandular tissue. Referring to FIG. 7, a left part of FIG. 7 illustrates a part of image blocks in the classified breast image. Image blocks 711, 713 and 715 are classified into the mammary glandular tissue type by the classifier, and an image block 721 is classified into the subcutaneous fat type by the classifier. After determining that at least two image blocks classified to the mammary glandular tissue type (i.e., the image blocks 711, 713 and 715) exist adjacent to the image block 721, the mammary glandular detection module 113 transforms the image block 721 into the mammary glandular tissue type through a filling up operation (step S750). A right part of FIG. 7 illustrates a part of the image blocks processed through the filling up operation, where the image blocks 711, 713, 715 and 721 all belong to the mammary glandular tissue type.

It should be noted that a decision mechanism of transforming the image block not belonging to the mammary glandular tissue type into the mammary glandular tissue type may also be determining whether one, two, or four image blocks belonging to the mammary glandular tissue type exist adjacent to the image block not belonging to the mammary glandular tissue type, though the present disclosure is not limited thereto.

Figure 8:
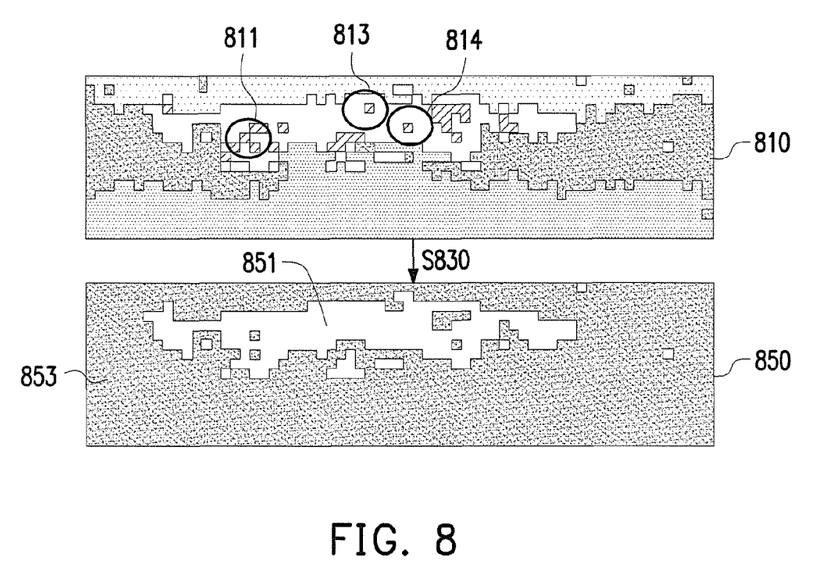
FIG. 8 is another example of filling up the mammary glandular tissue.

FIG. 8 is another example of filling up the mammary glandular tissue. Referring to FIG. 8, image blocks 811, 813, and 814 in a classified breast image 810 are not classified into the mammary glandular tissue type by the classifier. In step S830, because at least two image blocks belonging to the mammary glandular tissue type exist adjacent to each of image blocks 811, 813, and 814, the mammary glandular detection module 113 performs the filling up operation to the image blocks 811, 813 and 814 to transform the image blocks 811, 813, and 814 into the mammary glandular tissue type. A breast image 850 processed through the filling up operation can be separated into an image region 851 (presented in the white background color) belonging to the mammary glandular tissue type and an image region 853 (presented in black mesh points) not belonging to the mammary glandular tissue type (for example, the subcutaneous fat type, the shadow type, etc.). The image blocks 811, 813, and 814 in the breast image 810 all belong to the image region 851.

Figure 9:
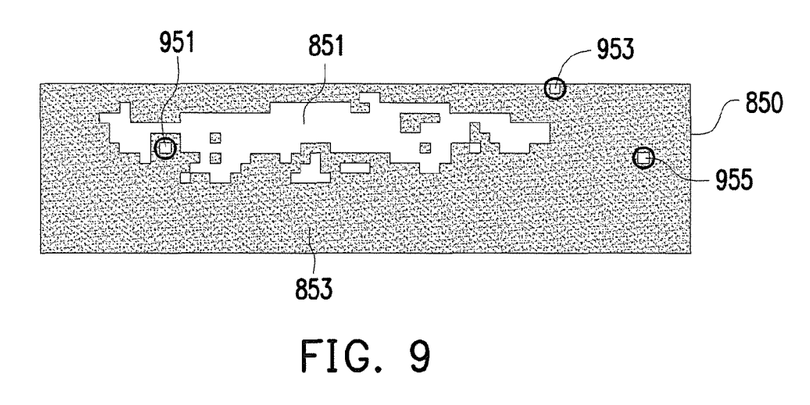
FIG. 9 is an example for removing noise blocks.

In an embodiment, the mammary glandular detection module 113 may further remove noise blocks in the mammary glandular tissue. To be specific, because a plurality of connected image blocks belonging to the mammary glandular tissue type probably exists in the classified breast image, the mammary glandular detection module 113 may determine an image region (for example, the image region 851 of FIG. 8) formed by one or more connected image blocks as a decision image region of the mammary glandular tissue type. Then, the mammary glandular detection module 113 takes the image blocks that are not connected to the decision image region and belong to the mammary glandular tissue type as noise blocks for removal (i.e., transform the similarity into the non-mammary glandular tissue type). For example, FIG. 9 is an example for removing the noise blocks. The breast image 850 of FIG. 9 includes image blocks 951, 953 and 955, which are not connected to the maximum image region 851 belonging to the mammary glandular tissue type, i.e. the noise blocks. The mammary glandular detection module 113 may perform a noise removing operation to transform the image blocks 951, 953 and 955 into the image region 853 not belonging to the mammary glandular tissue type.

Figure 10:
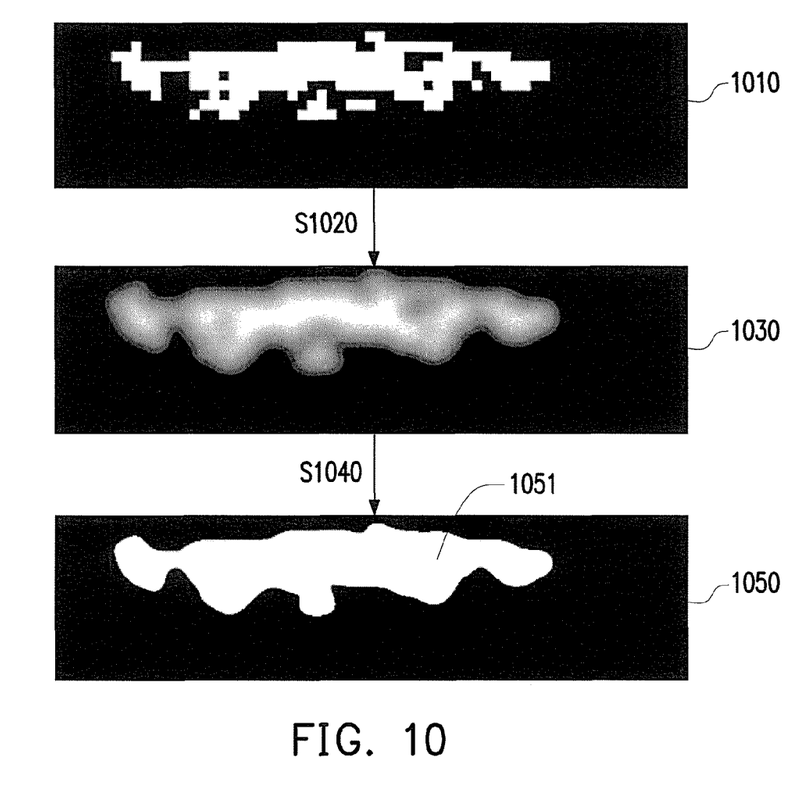
FIG. 10 is an example of mammary glandular tissue outline transform.

Then, the mammary glandular detection module 113 may further obtain a mammary glandular tissue outline. The mammary glandular detection module 113 may transform the mammary glandular tissue outline presented in image blocks into a smooth outline. For example, FIG. 10 is an example of mammary glandular tissue outline transform. Referring to FIG. 10, the mammary glandular detection module 113 performs erosion operation on a breast image 1010 (for example, the breast image processed through the noise removing operation), and blurs the breast image 1010 by using a Gaussian filter (step S1020) to form a breast image 1030. Then, the mammary glandular detection module 113 transforms the mammary glandular tissue into a thresholding breast image 1050 by using an Otsu thresholding method (also known as maximum between-class variance) (step S1040). A mammary glandular tissue region 1051 (presented in the white background color) in the thresholding breast image 1050 is the mammary glandular tissue finally determined by the mammary glandular detection module 113.

In an embodiment, in order to determine whether the breast is a dense breast (i.e., the mammary glandular tissue and connective tissue are relatively more and fat is relatively less), the density quantification module 116 may calculate a mammary glandular tissue area in each of the breast images, and calculate a mammary glandular tissue quantification value based on the mammary glandular tissue area in the breast image. To be specific, the density quantification module 116 respectively calculates the mammary glandular tissue area of each slice of breast image obtained by the mammary glandular detection module 113, and divides the mammary glandular tissue area of each slice of breast image by a total area of the respective slice of breast image to calculate a mammary glandular tissue density of each slice of breast image. The density quantification module 116 may average the mammary glandular tissue densities of all slices of the breast image to calculate the mammary glandular tissue quantification value. The density quantification module 116 may further determine whether the mammary glandular tissue quantification value exceeds a density threshold to determine whether the breast is the dense breast. Conversely, if the mammary glandular tissue quantification value does not exceed the density threshold, the breast is determined to be non-dense breast.

In another embodiment, the false positive comparison module 117 may use a computer-aided detection (CADe) system to detect at least one abnormal position, and compare the abnormal positions with the mammary glandular tissue in the corresponding breast image. To be specific, the false positive comparison module 117 may record a mammary glandular tissue position of the breast tissue in each slice of breast image obtained by the mammary glandular detection module 113. The processing unit 150 may obtain a suspicious lesion (for example, a tumor, a lump, etc.) position (i.e., the abnormal position) in the input breast image of the step S210 by additionally loading a CADe program or through an external CADe system. The false positive comparison module 117 compares the mammary glandular tissue position with the suspicious lesion position to determine whether the suspicious lesion position overlaps with the mammary glandular tissue position. According to clinical statistics, since most of the lesions grow along a gland, false positive (the CADe system determines the suspicious lesion to be a lesion, though it is not a lesion in fact) can be decreased by excluding the suspicious lesion that is not on the mammary glandular tissue position. In other words, if the false positive comparison module 117 determines that the suspicious lesion position overlaps with the mammary glandular tissue position, it can be further determined that the suspicious lesion position has an extremely high chance (for example, greater than 50%, 75%, 80%, etc.) to have a lesion, and physician may perform further diagnosis on the suspicious lesion position.

Moreover, since human milk is lactated by a mammary gland in the breast, a lactation yield relates to development and integrity of the mammary gland. In an embodiment, the lactation yield assessment module 118 may assess the lactation yield according to the quantification result of the density quantification module 116. The larger the mammary glandular tissue is, the higher the lactation yield is, and there is a positive correlation therebetween. For example, the lactation yield assessment module 118 may determine whether the mammary glandular tissue quantification value is greater than a lactation yield threshold, so as to determine whether a lactation yield of a testee is high. Alternatively, the lactation yield assessment module 118 may set lactation yield levels to 5, 7, or 10 levels, etc., and determine the lactation yield level corresponding to the mammary glandular tissue quantification value.

In another embodiment, the left and right breasts gland density symmetry measurement module 119 uses the density quantification module 116 to simultaneously quantify the mammary glandular tissue densities of the left and right breasts, and determines symmetry (for example, a difference proportion, etc.) by comparing the mammary glandular tissue densities of the left and right breasts. The left and right breasts gland density symmetry measurement module 119 may also simultaneously display density diagrams of mammary glandular tissue of the left and right breasts in a visual approach through a display unit (for example, the mammary glandular tissue densities adopt different colors to represent different density levels).

Figure 11:
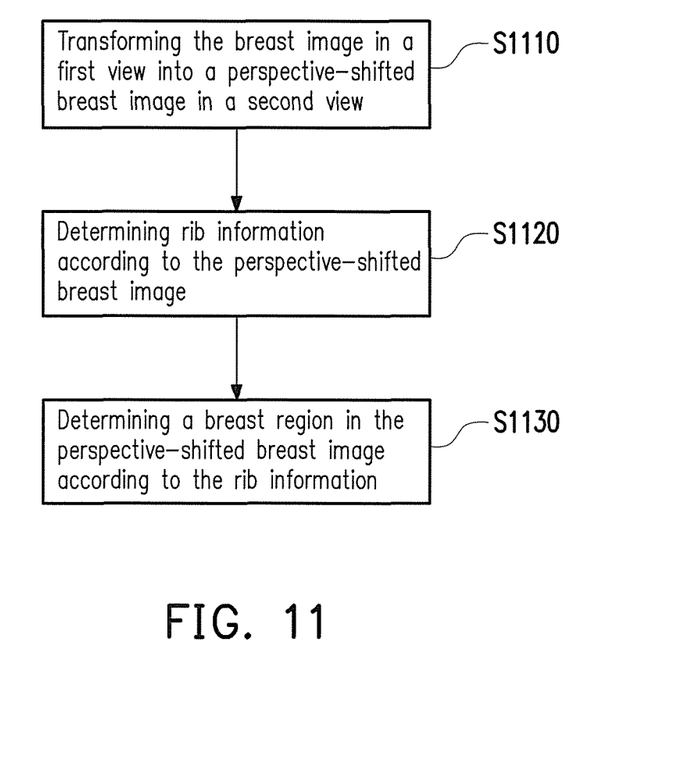
FIG. 11 is a flowchart illustrating a method for segmenting a breast region according to an embodiment of the present disclosure.

In yet another embodiment, after step S210, the medical image processing apparatus 100 may separate a breast region from the breast image before performing the operation of detecting the mammary glandular tissue of S230. FIG. 11 is a flowchart illustrating a method for segmenting a breast region according to an embodiment of the present disclosure. Referring to FIG. 11, the method of the present embodiment is adapted to the medical image processing apparatus 100 of FIG. 1. The method of the present embodiment is described below with reference of various components and modules of the medical image processing apparatus 100. Various steps of the method can be adjusted according to an actual implementation requirement, which is not limited by the present disclosure.

Figure 12A:
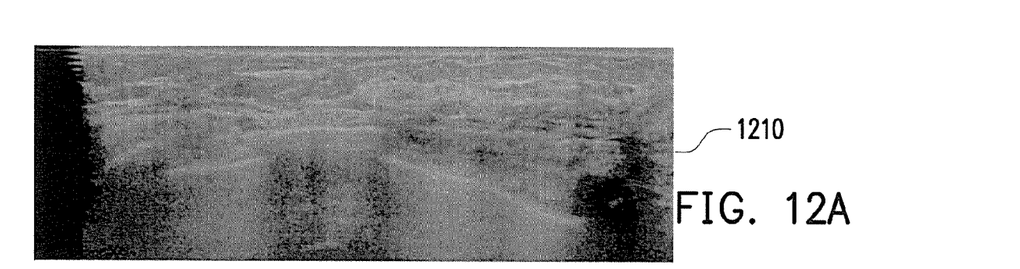
FIG. 12A is an example of a slice of breast image in the transverse view.

In step S1110, the breast region segmentation module 114 transforms the breast image in a first view into a perspective-shifted breast image in a second view. The first view is different from the second view. To be specific, an automated breast ultrasound image is generally scanned from regions below the collar bones to the nipples, and is usually presented in a transverse view. Referring to FIG. 12A, which is an example of a slice of breast image 1210 in the transverse view. Texture differences between different tissues are less obvious in the transverse view so it is difficult to separate the breast region since the tissues are hard to recognize.

Figure 12B:
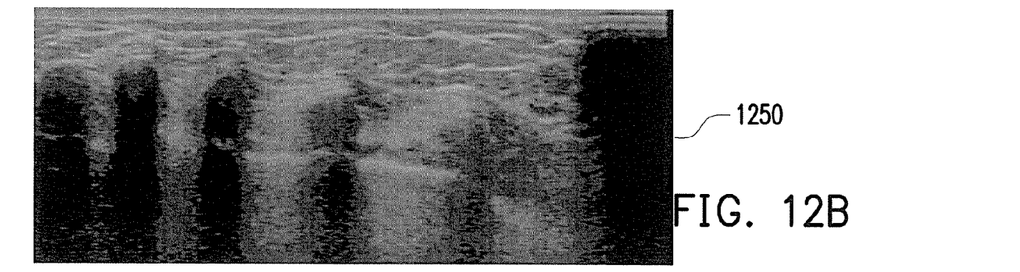
FIG. 12B is an example of transforming FIG. 12A into a perspective-shifted breast image in the sagittal view.

A pre-processing procedure is initially performed in the present embodiment in order to facilitate subsequent processing. In the present embodiment, the first view is the transverse view, and the second view is a sagittal view. In other words, after the at least one slice of breast image in the transverse view is obtained in step S210, the breast region segmentation module 114 transforms the breast images in the transverse view into perspective-shifted breast images in the sagittal view. Referring to FIG. 12B, which is an example of transforming FIG. 12A into a perspective-shifted breast image 1250 in the sagittal view. Compared to the transverse view shown in FIG. 12A, the sagittal view can provide a large amount of information for recognizing different tissue types (for example, rib, rib shadow (a black region under the rib in the image where the ultrasound cannot pass through), skin, etc.).

Next, the breast image segmentation module 114 can enhance a contrast ratio of the breast image by using an image enhancing filter (for example, a S-shaped (sigmoid) filter, a histogram equalization (HE)), so that a difference between a rib shadow region with decreased pixel intensity and other tissue with increased pixel intensity is more obvious.

In addition, the breast image segmentation module 114 can also perform a noise removal operation on the perspective-shifted breast image. For example, the breast region segmentation module 114 can perform smoothing on the perspective-shifted breast image by using an edge preserving filter and remove speckle noise by using an anisotropic diffusion filter.

Figure 13:
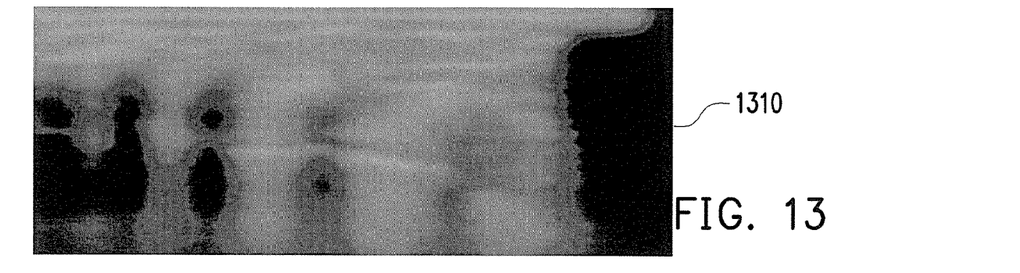
FIG. 13 is a schematic diagram illustrating an example of the perspective-shifted breast image of FIG. 12B after noise removal.

For example, FIG. 13 is a schematic diagram illustrating an example of the perspective-shifted breast image of FIG. 12B after noise removal. Referring to FIG. 13, a perspective-shifted breast image 1310 after regulation (noise removal) is processed through the S-shaped and anisotropic diffusion filters, and has the enhanced contrast ratio and the reduced speckle noise.

After the pre-processing is completed, the breast region segmentation module 114 can obtain a blurry image with higher contrast ratio and lower noise compared to the image before processing. In step S1120, the breast region segmentation module 114 determines rib information according to the perspective-shifted breast image (after regulation). To be specific, the present embodiment combines local information with global information to segment a chest wall line. The local information came from a single slice, and the global information came from the whole set of the perspective-shifted breast images.

In an embodiment, the rib information includes rib shadow information. With assistance of the rib shadow information, a chest cage may be observed. The global information is still needed since each slice of perspective-shifted breast image provides only a fragment of the rib shadow information. The breast region segmentation module 114 can calculate projection values of pixels in all the perspective-shifted breast images, and determine a chest wall reference line according to the projection values of the pixels.

In the present embodiment, the breast region segmentation module 114 can obtain the projection values by projecting the pixels corresponding to the same coordinate location in different slices of perspective-shifted breast image along a slice axis with use of a mean projection method, and calculate mean intensity values corresponding to the same coordinate location in all slices of perspective-shifted breast image. On the same coordinate location, the mean intensity value of each pixel is used as a threshold for classifying a projection result into two types (for example, a first type pixel and a second type pixel). The breast region segmentation module 114 can determine whether an intensity value of each pixel in each slice of breast image is greater than the mean intensity value of the corresponding coordinate location, and preserves and/or records the pixels having the intensity value greater than the mean intensity value of the corresponding coordinate location (hereinafter, also known as the first type pixel). If the intensity value of one specific pixel (hereinafter, also known as the second type pixel) is not greater than the mean intensity value of the corresponding coordinate location, the breast region segmentation module 114 discards the second type pixel and/or records the second type pixel by ways of numbers, symbols, codes and type different from those used for recording the first type pixel. For example, the breast region segmentation module 114 sets the first type pixel as 1 and sets the second type pixel as 0.

Figure 14:
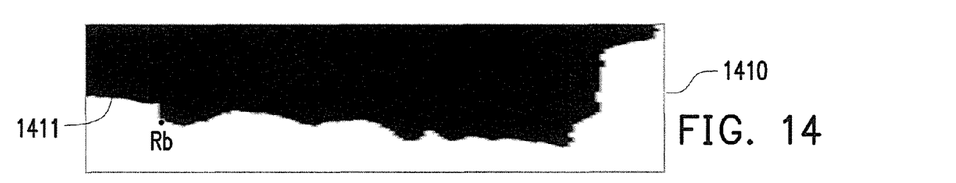
FIG. 14 is a schematic diagram illustrating an example of a chest wall reference line formed after filtering the perspective-shifted breast image of FIG. 13 by a mean projection method and binarization.

Accordingly, all fragments of the rib shadow information from each slice are combined to generate global chest information (for example, an outline of the chest cage and a rib distribution) so the chest wall reference line may be determined. For example, FIG. 14 is a schematic diagram illustrating an example of a chest wall reference line 1411 formed after filtering the perspective-shifted breast image of FIG. 13 by a mean projection method and binarization. Referring to FIG. 14, in a perspective-shifted breast image 1410 filtered by the mean projection method, the white region represents all of the rib locations in the chest, describing a traverse region of rib locations (all of the ribs are included in this region, and global rib shadow location information is included). On the other hand, the black region represents a chest region, which describes a distribution region of all the breast tissues in the breast image. A boundary line of the white and black regions is the chest wall reference line 1411.

In another embodiment, the rib information includes the rib shadow information. The breast region segmentation module 114 can determine the rib shadow information in each perspective-shifted breast image through an image segmentation method (for example, the Otsu thresholding method, a region growing method, etc.). The rib shadow information includes the chest wall line.

In the present embodiment, the breast region segmentation module 114 separates the rib shadow region from the perspective-shifted breast image (after regulation through the S-shaped and anisotropic diffusion filters), and performs a clustering based image thresholding process to separate the perspective-shifted breast image into a foreground image (the rib shadow region) and a background image (other tissue). A thresholding value used in the image thresholding process is maximum between-class variance.

Figure 15:
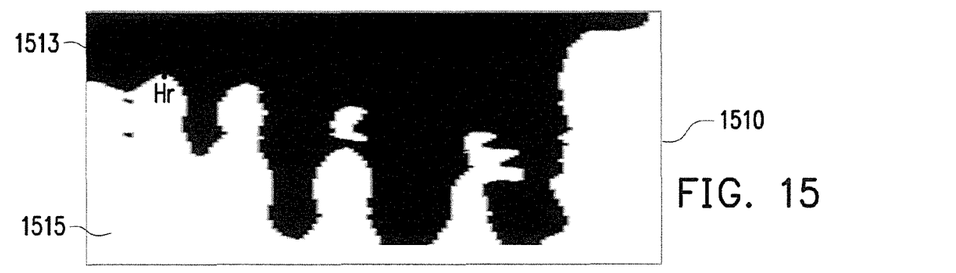
FIG. 15 is a schematic diagram illustrating an example of a rib map formed after performing the Otsu thresholding method on the perspective-shifted breast image of FIG. 13.

For example, FIG. 15 is a schematic diagram illustrating an example of a rib map formed after performing the Otsu thresholding method on the perspective-shifted breast image of FIG. 13. Referring to FIG. 15, in a thresholding perspective-shifted breast image 1510, a rib shadow region 1515 presented by the white background color may be considered as the rib map, and an other tissue region 1513 may be presented by the black background color. The local rib shadow information (i.e., the local information) obtained form each slice of perspective-shifted breast image includes local rib locations (information regarding length and width of rib). Regions (intercostal spaces) between these ribs do not belong to the breast region and will be removed in the subsequent procedure.

In step S1130, the breast region segmentation module 114 determines a breast region in the perspective-shifted breast image according to the rib information. To be specific, after aforesaid procedure, the breast region segmentation module 114 can obtain the global information and the local information for each slice of perspective-shifted breast image, so as to distinguish the chest wall according these information. In an embodiment, the breast region segmentation module 114 can regulate the chest wall line in each of the perspective-shifted breast images according to the chest wall reference line.

Taking FIG. 14 and FIG. 15 for example, the breast region segmentation module 114 can record a highest point Hr of the rib shadow in the rib map (for example, as shown in FIG. 15) for each slice. The highest point Hr describes a minimum chest thickness in this slice of perspective-shifted breast image. The breast region segmentation module 114 obtains the coordinate of the highest point Hr in the perspective-shifted breast image, records row/column numbers corresponding to the coordinate from the rib map, and searches a coordinate location (a reference point Rb) with the row/column numbers corresponding to the chest wall reference line 1411 in FIG. 14.

The breast region segmentation module 114 can align the chest wall reference line 1411 with the corresponding row/column numbers and transplants the pixels of the chest wall line on each slice of rib map according to the highest point Hr and the reference point Rb. In other words, the breast region segmentation module 114 makes the perspective-shifted breast images 1410 and 1510 overlaps, aligns the reference point Rb with the highest point Hr, and regulates the pixels of the row/column numbers corresponding to the rib shadow region 1515 to the chest wall reference line 1411 according to the boundary line of the other tissue region 1513 and the chest wall reference line 1411. For the boundary line of the rib shadow region 1515 and the chest wall reference line 1411, an outline of the corresponding row/column numbers is preserved. Accordingly, the chest wall line may be regulated to remove the intercostal spaces from the other tissue region 1513.

Figure 16A:
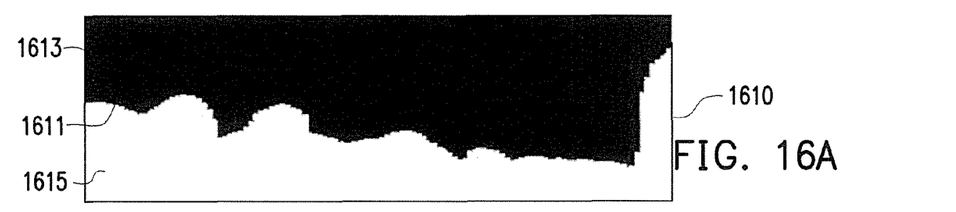
FIG. 16A is a schematic diagram illustrating an example of the perspective-shifted breast image after regulation according to the chest wall reference line.

For example, FIG. 16A is a schematic diagram illustrating an example of the perspective-shifted breast image 1510 after regulation according to the chest wall reference line 1411. Referring to FIG. 16A, in a perspective-shifted breast image 1610, a boundary line between the white (representing a chest cavity region 1615 (for example, including rib, rib shadow, intercostal spaces, etc.)) and black (representing a chest region 1613 yet including pectoral muscles) regions is a chest wall line 1611 after regulation.

Then, the breast region segmentation module 114 removes a pectoral muscles portion from the regulated perspective-shifted breast image to determine the breast region. To be specific, according to the average thickness of pectoral muscles (approximately 1.5 to 2.0 cm), the breast region segmentation module 114 can remove the pectoral muscles portion from the chest region 1613 by subtracting the average thickness of pectoral muscles from the bottom of a thickness of the chest region (for example, the chest region 1613 in FIG. 16A), so as to regulate the chest wall line 1611 to be a chest wall line 1631 (for example, shifting upwardly).

Figure 16B:
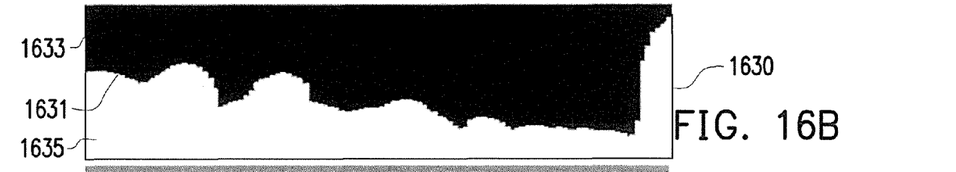
FIG. 16B is a schematic diagram illustrating an example of the perspective-shifted breast image after regulation according to the average thickness of pectoral muscles.

The pectoral muscles portion may be removed by subtracting the average thickness of the pectoral muscles portion from a height of the chest wall line after regulation (for example, the chest wall line 1611), so as to further regulate the chest wall line. For example, FIG. 16B is a schematic diagram illustrating an example of the perspective-shifted breast image 1610 after regulation according to the average thickness of pectoral muscles. In the perspective-shifted breast image 1630, the boundary line of the white (representing a non-chest region 1635 (for example, including rib, rib shadow, intercostal space, pectoral muscles etc.) and black (representing a chest region 1633) regions is the chest wall line 1631 after regulation. That is, the chest wall line 1631 is formed by subtracting the average thickness of pectoral muscles from the thickness of the chest region 1613 in FIG. 16A.

In some embodiments, the breast region segmentation module 114 may further eliminate a skin portion in the chest region (for example, the chest region 1633 in FIG. 16B). Taking FIG. 16B for example, the breast region segmentation module 114 can regulate the chest region 1633 by subtracting a skin thickness of 1.5 to 1.7 mm from the top of the chest region 1633.

Figure 16C:
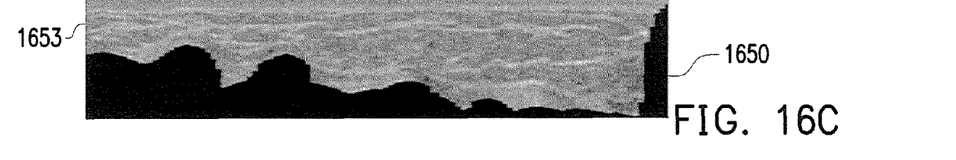
FIG. 16C is a schematic diagram illustrating an example of obtaining a chest region of the perspective-shifted breast image in FIG. 12B.

Then, the breast region segmentation module 114 may remove regions below the chest wall line (for example, the chest wall line 1631 in FIG. 16B) in the perspective-shifted breast image already transformed to the sagittal view according to the chest region (for example, the chest region 1633 in FIG. 16B), so as to obtain the perspective-shifted breast image including only the chest region. Referring to FIG. 16C, which is a schematic diagram illustrating an example of obtaining a chest region of the perspective-shifted breast image 1250 in FIG. 12B. In a perspective-shifted breast image 1650, only the image of a chest region 1653 is preserved.

In yet another embodiment, the breast region segmentation module 114 can restore the breast image back to the transverse view or breast images in other views to facilitate the subsequent procedures.

In some embodiments, the processing unit 150 may further present one of the mammary glandular tissue quantification value, the dense breast determination result, the suspicious lesion position, the mammary glandular tissue position, the lactation yield, the breast images in different views, the density diagrams of mammary glandular tissue of the left and right breasts and a lesion prompt message, or a combination thereof through the display unit, so as to assist the physician to clearly learn an inspection situation.

In summary, the medical image processing apparatus and the breast image processing method thereof of the present disclosure are adapted to detect the mammary glandular tissue in the breast image based on texture characteristic analysis such as gray-level co-occurrence matrix (GLCM), Markov random field (MRF), or Gabor filter, etc., and further calculate mammary glandular tissue quantification value according to the detected mammary glandular tissue, and assist to confirm the suspicious lesion detected by the CADe system. In this way, the embodiments of the present disclosure may improve accuracy for detecting the mammary glandular tissue, and efficiently reduce false positive of the CADe system. On the other hand, the embodiments of the present disclosure can further assist the subsequent density analysis by separating the breast region in the breast image according to the rib information.

It will be apparent to those skilled in the art that various modifications and variations can be made to the structure of the present invention without departing from the scope or spirit of the present disclosure. In view of the foregoing, it is intended that the present disclosure cover modifications and variations of this disclosure provided they fall within the scope of the following claims and their equivalents.

What is claimed is:

1. A breast image processing method, adapted to a medical image processing apparatus, the breast image processing method comprising:
    obtaining at least one breast image by an image input module;
    detecting mammary glandular tissue in each of the at least one breast image through a mammary glandular tissue detector, wherein the mammary glandular tissue detector is based on texture characteristic analysis;
    calculating a mammary glandular tissue density in the at least one breast image;
    detecting at least one abnormal position in the at least one breast image by using a computer-aided detection (CADe) system; and
    comparing the at least one abnormal position with the mammary glandular tissue position in the at least one breast image by a false positive comparison module to determine whether the at least one abnormal position overlaps with the mammary glandular tissue position.

2. The breast image processing method as claimed in claim 1, wherein before the step of detecting the mammary glandular tissue in each of the at least one breast image through the mammary glandular tissue detector, the method further comprises:
    separating content of a plurality of breast training images into a plurality of characteristic types, wherein the characteristic types comprise a mammary glandular tissue type, a subcutaneous fat type, a retromammary fat and pectoralis muscle type, and a shadow type;
    performing the texture characteristic analysis on a plurality of image blocks in the breast training images; and
    training a classifier based on the texture characteristic analysis of each of the image blocks for the characteristic types, wherein the classifier for the mammary glandular tissue type is taken as the mammary glandular tissue detector.

3. The breast image processing method as claimed in claim 1, wherein the step of detecting the mammary glandular tissue in each of the at least one breast image through the mammary glandular tissue detector comprises:
    filling up the mammary glandular tissue in each of the at least one breast image;
    removing noise blocks in the mammary glandular tissue; and
    obtaining an outline of the mammary glandular tissue.

4. The breast image processing method as claimed in claim 1, wherein after the step of detecting the mammary glandular tissue in each of the at least one breast image through the mammary glandular tissue detector, the method further comprises:
    calculating a mammary glandular tissue area in each of the at least one breast image; and
    calculating a mammary glandular tissue quantification value based on the mammary glandular tissue area in the at least one breast image.

5. The breast image processing method as claimed in claim 1, wherein the step of detecting the mammary glandular tissue in each of the at least one breast image through the mammary glandular tissue detector comprises:
    transforming the at least one breast image in a first view into at least one perspective-shifted breast image in a second view, wherein the first view is different from the second view;
    determining rib information according to the at least one perspective-shifted breast image; and
    determining a breast region in the at least one perspective-shifted breast image according to the rib information.

6. The breast image processing method as claimed in claim 5, wherein the rib information comprises a chest wall reference line and rib shadow information, and the step of determining the rib information according to the at least one perspective-shifted breast image comprises:
    calculating projection values of a plurality of pixels in all of the at least one perspective-shifted breast image;
    determining the chest wall reference line according to the projection values of the pixels; and
    determining the rib shadow information in each of the at least one perspective-shifted breast image through an image segmentation, wherein the rib shadow information comprises a chest wall line.

7. The breast image processing method as claimed in claim 6, wherein the step of determining the breast region in the at least one perspective-shifted breast image according to the rib information comprises:
    regulating the chest wall line in each of the at least one perspective-shifted breast image according to the chest wall reference line; and
    removing a pectoral muscles portion from the regulated at least one perspective-shifted breast image to determine the breast region.

8. The breast image processing method as claimed in claim 5, wherein the first view is a transverse view and the second view is a sagittal view, and the step of transforming the at least one breast image in the first view into the at least one perspective-shifted breast image in the second view comprises:
    transforming the at least one breast image in the transverse view into at least one perspective-shifted breast image in the sagittal view.

9. A medical image processing apparatus, comprising:
    a storage unit, storing at least one breast image, and recording a plurality of modules; and
    a processing unit, coupled to the storage unit, accessing and executing the modules recorded in the storage unit, and obtaining at least one abnormal position in the at least one breast image by using a computer-aided detection (CADe) system, wherein the modules comprise:
    an image input module, obtaining the at least one breast image;
    a mammary glandular detection module, detecting mammary glandular tissue in each of the at least one breast image through a mammary glandular tissue detector, wherein the mammary glandular tissue detector is based on texture characteristic analysis;
    a density quantification module, calculating a mammary glandular tissue density in the at least one breast image; and
    a false positive comparison module, comparing at least one abnormal position with the mammary glandular tissue position in the at least one breast image to determine whether the at least one abnormal position overlaps with the mammary glandular tissue position.

\* \* \* \* \*